Figure 1:
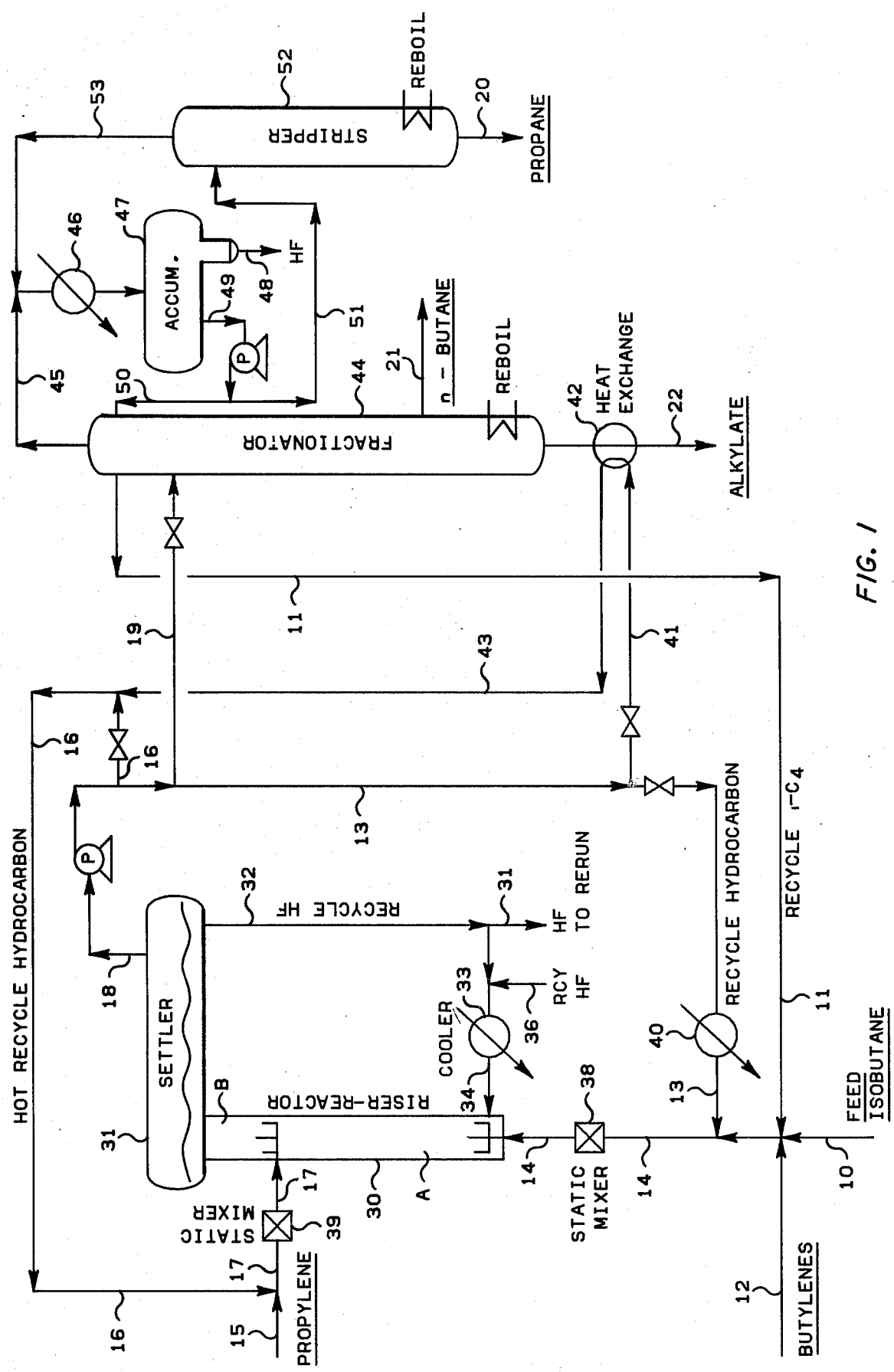

United States Patent [19]

Makovec et al.

[11] 4,161,497

[45] Jul. 17, 1979

[54] HF ALKYLATION INTRODUCING SEPARATE OLEFINS IN VERTICALLY EXTENDED REACTOR

[75] Inventors: Donald J. Makovec; Thomas Hutson, Jr., both of Bartlesville, Okla.

[73] Assignee: Phillips Petroleum Company, Bartlesville, Okla.

[21] Appl. No.: 840,424

[22] Filed: Oct. 7, 1977

[51] Int. Cl.² .............................................. C07C 3/54
[52] U.S. Cl. .................................... 585/714; 585/716; 585/719
[58] Field of Search .................................... 260/683.48
[56] References Cited

U.S. PATENT DOCUMENTS

| 3,080,438 | 3/1963 | Sailors | 260/683.48 |
|---|---|---|---|
| 3,169,152 | 2/1965 | Van Pool et al. | 260/683.48 |
| 3,169,153 | 2/1965 | Walker et al. | 260/683.48 |
| 3,246,047 | 4/1966 | Chapman et al. | 260/683.48 |
| 3,515,770 | 6/1970 | Tregilgas | 260/683.48 |
| 3,755,492 | 8/1973 | Anderson | 260/683.48 |
| 3,787,518 | 1/1974 | Anderson | 260/683.48 |

Primary Examiner—George Crasanakis

[57] ABSTRACT

An improved HF alkylation process comprising, in series, HF and isoparaffin flow and parallel injection of at least two different olefins into a vertically extended reaction zone coupled with recycle of some of the alkylation hydrocarbon effluent to each point of olefin introduction into the alkylation zone. The improved alkylation system allows minimum sized fractionation and extremely high isoparaffin/olefin ratios with temperature control of the reaction at each olefin injection.

6 Claims, 2 Drawing Figures

HF ALKYLATION INTRODUCING SEPARATE OLEFINS IN VERTICALLY EXTENDED REACTOR

This invention relates to an improved process for alkylation. In accordance with another aspect, this invention relates to an improved process for alkylating an isoparaffin with a plurality of olefins and the introduction of recycle hydrocarbon separated from the alkylation effluent into the reaction zone at each olefin injection. In accordance with a further aspect, this invention relates to an improved alkylation process having series HF and isoparaffin flow together with parallel injection of different olefins at spaced locuses along a vertically extended reaction zone and the introduction of recycle hydrocarbon effluent at each olefin injection. In accordance with a further aspect, this invention relates to an improved HF alkylation process comprising series HF and isoparaffin flow, parallel injection of at least two different olefins at spaced points along the vertically extended reaction zone, with a lighter olefin introduced downstream from a heavier olefin, and recycle of some of the hydrocarbon effluent to each point of olefin injection into the reaction zone.

The alkylation of an isoparaffin such as isobutane or isopentane with olefins such as propylene, butylenes, and amylenes has been practiced utilizing various alkylation catalysts, particularly HF acid. In applications where more than one olefin is to be reacted with an isoparaffin it is customary to either inject both olefins into a reactor, along with the isoparaffin, or to conduct two separate alkylation steps in different reactors. Some prefer alkylating in separate reactors with different olefins because a higher yield and higher quantity alkylate can be produced in each instance. This is due to the fact that optimum reaction conditions are different for different light olefins such as propylene, butylenes, and amylenes. This invention is concerned with a method and apparatus for alkylating an isoparaffin with two or more light olefins in a single reactor which results in a high yield of high quality alkylate. The present invention relates to an improved alkylation having parallel injection of a plurality of different olefins for increasing the alkylate octane number by recycling a portion of the alkylation hydrocarbon effluent prior to fractionation at each olefin injection to obtain desirable olefin dilution plus maintaining a high isoparaffin to olefin ratio along the length of a vertically extended reaction zone.

Accordingly, an object of this invention is to provide an improved process for alkylating an isoparaffin with a plurality of olefins in a single reaction zone.

A further object of this invention is to provide a more economical process requiring less fractionation equipment for alkylating an isoparaffin with a plurality of olefins.

Another object of this invention is to provide a process which produces an improved yield and quality of alkylate.

Other objects, aspects, and the several advantages of this invention will be apparent to those skilled in the art upon a study of this disclosure, the drawings and appended claims.

According to the invention, an improved HF alkylation process is provided comprising the spaced introduction of different olefins along a vertically extended reaction zone and recycle of a portion of the total alkylation hydrocarbon effluent for introduction at each olefin injection.

The instant alkylation process system allows minimum sized fractionation and extremely high isoparaffin to olefin ratios with temperature control of the reaction at each olefin injection.

In accordance with one specific embodiment, an improved HF alkylation process is provided comprising series HF and isoparaffin flow, parallel injection of different olefins at spaced points or locuses along a vertically extended alkylation reaction zone, and recycle of some of the alkylation hydrocarbon effluent separated from the alkylation process effluent prior to fractionation to each olefin injection.

In an embodiment, heavier olefin is introduced into a vertically extended reaction zone at the inlet end and at least one different lighter olefin is introduced at an intermediate locus along the vertically extended alkylation reaction zone and some of the hydrocarbon effluent separated prior to fractionation is recycled to each point of olefin injection.

In one embodiment, a butylene is introduced at the inlet end of the alkylation zone and propylene is introduced into the reaction zone at an intermediate point.

In another embodiment, propylene is introduced at the inlet end of the alkylation zone and a butylene is introduced into the reaction zone at an intermediate point.

In general, any of the conventional catalytic alkylation reactions can be carried out by the method of the present invention. Thus, the alkylation reaction can comprise reaction of an isoparaffin with an olefin or other alkylatable material carried out in the presence of a suitable alkylation catalyst. Suitable olefins include propylene, butenes, pentenes, hexenes, and the like. Suitable isoparaffins include isobutane, isopentane, and the like. A wide variety of alkylation catalysts can be employed in the alkylation reaction, but HF acid is presently preferred.

The alkylation reaction can be carried out under a wide range of conditions, but ordinarily sufficient pressure is used to maintain liquid phase conditions and a temperature sufficient to form alkylate. In the present invention, when a butylene is charged to the inlet end of the alkylation zone and propylene is charged to a point downstream, the temperature at the inlet end of the vertically extended reaction zone ranges from about 40° F. to about 100° F., a pressure of about 140 to about 200 psig, a total isoparaffin/olefin volume ratio of about 10 to 1 to about 100 to 1, an HF to total hydrocarbon volume ratio of about 5 to 1 to about 1 to 5, and a residence time in the range of about 20 to about 120 seconds. The amount of total hydrocarbon separated from the alkylation effluent and recycled to the inlet end of the reaction zone will be sufficient to provide a total hydrocarbon to olefin volume ratio of about 10 to 1 to about 100 to 1.

The conditions in the alkylation zone downstream from the inlet end in proximity of injection of different olefins will vary from those at the inlet end in that the temperature will range from about 60° F. to about 120° F. and sufficient pressure to maintain liquid phase conditions, e.g., about 140 to about 200 psig. The total isoparaffin to olefin volume ratio will range from about 10 to 1 to about 100 to 1, the HF to total hydrocarbon volume ratio will range from about 5 to 1 to about 1 to 5, and the residence time will range from about 20 to about 120 seconds. The amount of total hydrocarbon separated from the alkylation effluent and recycled to the intermediate locuses of the alkylation reaction zone is sufficient to provide a total hydrocarbon to different olefin volume ratio of about 2 to 1 to about 50 to 1.

In the present invention, when propylene is charged to the inlet end of the alkylation zone and a butylene is charged to a point downstream, the temperature at the inlet end of the vertically extended reaction zone ranges from about 60° F. to about 120° F. and sufficient pressure to maintain liquid phase conditions, e.g., about 140 to about 200 psig. The total isoparaffin to olefin volume ratio will range from about 10 to 1 to about 100 to 1, the HF to total hydrocarbon volume ratio will range from about 5 to 1 to about 1 to 5, and the residence time will range from about 20 to about 120 seconds. The amount of total hydrocarbon separated from the alkylation effluent and recycled to the inlet end of the reaction zone will be sufficient to provide a total hydrocarbon to olefin volume ratio of about 10 to 1 to about 100 to 1.

The conditions in the alkylation zone downstream from the inlet end in proximity of the injection of different olefins will vary from those at the inlet end in that the temperature range will be from about 40° F. to about 100° F., a pressure sufficient to maintain liquid phase conditions, e.g., about 140 to about 200 psig. The total isoparaffin to olefin volume ratio will range from about 10 to 1 to about 100 to 1, the HF to total hydrocarbon volume ratio will range from about 5 to 1 to about 1 to 5, and the residence time will range from about 20 to about 120 seconds. The amount of total hydrocarbon separated from the alkylation effluent and recycled to the intermediate locuses of the alkylation reaction zone is sufficient to provide a total hydrocarbon to different olefin volume ratio of about 2 to 1 to about 50 to 1.

The hydrocarbon separated and recycled from the alkylation effluent comprises total hydrocarbon prior to fractionation and a sufficient amount of the hydrocarbon is separated and recycled to each olefin injection to provide the amount of recycle hydrocarbon set forth above. The recycle hydrocarbon can enter the alkylation zone with the olefin at each point of injection or separately. The recycle hydrocarbon is introduced into the reaction zone in such a way so that it is present as reaction heat removal liquid when the alkylation reaction is occurring. The temperature of the recycle hydrocarbon can be adjusted prior to injection into the alkylation reaction zone so as to provide temperature control of the reaction at each olefin injection.

More than two olefin addition loci can be used.

Figure 2:
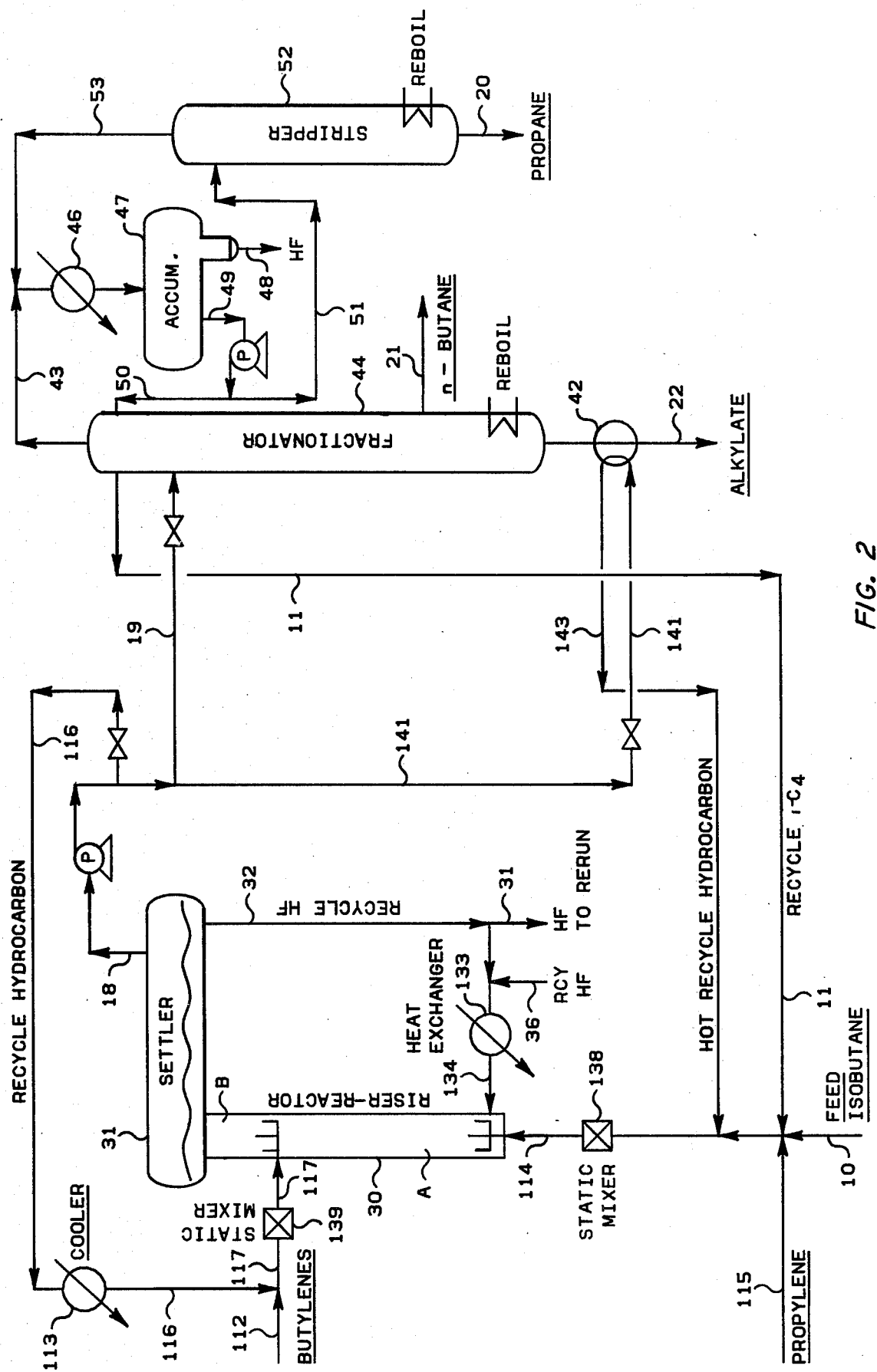

A better understanding of the invention will be had upon reference to the accompanying schematic drawings which embody two different embodiments for effecting the invention, wherein:

FIG. 1 is one embodiment of an alkylation operation wherein a butylene is introduced at the inlet end of a vertically extended reaction zone and propylene is introduced at an intermediate locus along the length of the reaction zone and the portion of the total alkylation hydrocarbon effluent is recycled to each point of olefin injection; and FIG. 2 is another embodiment of an alkylation operation wherein propylene is introduced at the inlet end of the alkylation zone and a butylene is introduced into the reaction zone at an intermediate point and a portion of total alkylation hydrocarbon effluent is recycled to each point of olefin introduction.

Referring to FIG. 1, a tubular riser-reactor 30 is connected at the outlet end with acid settler 31 which is provided with a take-off line 18 for alkylate (hydrocarbon phase). An acid return line 32 connects with the bottom section of settler 31 and can be passed through acid cooler 33 and then line 34 for introduction into inlet end of riser-reactor 30. Some of the recycle HF acid can be withdrawn through line 35 and passed to a rerun unit and returned to the process by way of line 36.

Feed isobutene in line 10 is mixed with butylene introduced by line 12 and recycle isobutane by line 11, and the combined stream is passed by way of line 14 through static mixer 38 and introduced into inlet end of riser-reactor 30 by way of line 14. Recycle hydrocarbon removed from settler 31 is combined with the feed isobutane and butylenes by line 13. The alkylation feed together with recycle hydrocarbon are contacted with HF acid at the inlet end of riser-reactor 30 and subjected to alkylation conditions such that alkylate is formed and is passed through riser-reactor 30 to the outlet end and introduced into a lower portion of settler 31.

Propylene in line 15 is combined with recycle hydrocarbon introduced by line 16 and passed by way of line 17 through static mixer 39 and introduced into an intermediate portion of riser-reactor 30. Propylene together with isobutane introduced through line 17 into the reaction mixture in riser-reaction 30 are subjected to conditions such that additional alkylate is formed and is passed along with previously formed alkylate into a lower portion of settler 31.

The alkylation reaction effluent introduced into settler 31 is allowed to phase separate into an upper hydrocarbon phase and a lower HF acid phase. The upper hydrocarbon phase is removed from settler 31 by way of line 18 and a portion can be recycled directly into an intermediate portion of riser-reactor 30 by way of line 16. Another portion of the alkylation hydrocarbon effluent can be passed by way of line 13 to the inlet end of riser-reactor 30. The recycle hydrocarbon in line 13 can be cooled to a desired temperature by passing same through heat exchanger 40. When it is desired to adjust the temperature of the recycle hydrocarbon in line 16, a portion of the hydrocarbon phase in line 13 can be passed through valved line 41 and heat exchanged with alkylate in line 22 by passage through heat exchanger 42 and returned to line 16 by way of line 45.

The remainder of the hydrocarbon effluent separated from settler 31 is passed by way of line 19 and introduced into fractionator 44 wherein the hydrocarbon effluent is subjected to such fractionation conditions as to take overhead by line 45 propane and lighter materials which are condensed by cooler 46 and the cooled condensate is passed to accumulator 47. HF is withdrawn from a lower portion of accumulator 47 by way of line 48. Hydrocarbon is withdrawn by line 49 and passed in part by line 50, as reflux, to an upper portion of fractionation zone 44. Normal butane is withdrawn from zone 44 by way of line 21 and alkylate product by way of line 22.

The remainder of the hydrocarbon removed from accumulator 47 not returned to column 44 as reflux is passed by way of line 51 to stripper 52 wherein HF and other light materials are removed overhead by way of line 53. Propane is removed as bottoms by way of line 20.

EXAMPLE

An alkylation operation based on a calculated example from pilot plant runs is carried out in an apparatus similar to that shown in FIG. 1 with the conditions described below.

In the inlet portion of the riser-reactor 30, which is identified as Zone A, the following conditions are used:

| Reaction Zone A: | |
| --- | --- |
| Pressure, psig | 160 |
| Temperature, °F. | 90 |
| Total IC$_4$/Butylenes Vol. Ratio | 38:1 |
| Recycle Hydrocarbon/Butene Vol. Ratio | 18.7:1 |
| HF to Total Hydrocarbon Vol Ratio | 1.5:1 |
| Residence Time, seconds | 40 |

The conditions obtained in Zone B, which is downstream from the point of injection of propylene in riser-reactor 30, are as follows:

| Reaction Zone B: | |
| --- | --- |
| Pressure, psig | 160 |
| Temperature, °F. | 110 |
| Total IC$_4$/Propylene Vol. Ratio | 56 |
| Recycle Hydrocarbon/Propylene Vol. Ratio | 13:1 |
| HF to Total Hydrocarbon Vol. Ratio | 1.23:1 |
| Residence Time, seconds | 40 |

The alkylation operation results in the following flow pattern:

| Stream | | Barrels/Minute |
| --- | --- | --- |
| (10) | Total Fresh IC$_4$ | 1.40 |
| (11) | Recycle IC$_4$ | 13.00 |
| (12) | Butylenes | 0.56 |
| (13) | Recycle Hydrocarbon | 10.50 |
| (14) | Total Feed to Reaction Zone A | 25.46 |
| (15) | Propylene | 0.44 |
| (16) | Recycle Hydrocarbon | 5.25 |
| (17) | Total Outside Feed | 5.69 |
| (—) | Feed from Zone A | 25.26 |
| (—) | Total feed to Reaction Zone B | 30.95 |
| (18) | Hydrocarbon from Settler | 30.64 |
| (19) | To Fractionation | 14.89 |
| (20) | Propane Yield | 0.04 |
| (21) | Normal Butane Yield | 0.07 |
| (22) | Alkylate Yield | 1.78 |
| | RON (Clear) | 94.3 |

Based upon the above example, the yield of mixed alkylate obtained is 178 volume percent of olefin feed, and this is found to have a Research Octane rating (clear) of 94.3.

Referring now to FIG. 2, operating with the same amounts of charge materials as set out in the above example, but charging propylene to the inlet end and a butylene to the intermediate locus of the alkylation zone, and operating the inlet end at 160 psig, and 110° F., and operating the intermediate locus at 160 psig, and 90° F., the total alkylate octane number (RON clear) was 95.4. It is believed that, when operating with proplene first and then butylenes later, FIG. 2, the intermediate zone, being at a lower temperature than the propylene alkylation inlet zone, does not cause degradation of the propylene alkylate; while it is believed that when adding butylenes first and propylene later, FIG. 1, the intermediate zone, now being at a higher temperature than the butylene alkylation inlet zone, does cause some degradation of the butylene alkylate.

Again referring to FIG. 2, feed isobutane 10, recycle isobutane 11, and propylene 115 are charged to the inlet end A of reactor 30, along with a portion of the hydrocarbon phase 143 from settler 30, which portion is passed via line 18, line 141, is indirectly heated in 42, and added to the inlet end of the alkylation reactor 30 via line 143. Recycle HF 32 is passed via heater 133 and line 134 into the lower or inlet end of reactor 30 via static mixer 138 and line 114. Isobutane is alkylated with propylene in this zone A at the relatively high temperature, as desired for optimum octane. Butylene or butylenes 112 are added to the reactor 30 zone B along with a portion of the hydrocarbon phase 116 from settler 31, which portion is passed via indirect cooler 113 into the butylenes feed 112, and the blend is passed via static mixer 139 and line 117 into zone B, operated at the relatively low temperature, as desired for optimum octane. The other numerals on FIG. 2 correspond with those on FIG. 1.

We claim:

1. A process for alkylating an isoparaffin with a lighter and a heavier olefin in the presence of HF acid in a vertically extended reactor comprising:
   (a) introducing a liquid mixture comprising an isoparaffin, said lighter olefin, and said catalyst into the lower end portion of said reactor to pass said mixture upwardly through said reactor;
   (b) introducing said heavier olefin into said reactor at an intermediate section in said reactor substantially downstream of the place of introduction of said olefin in (a);
   (c) passing said mixture of (b) through said reactor at suitable conditions of temperature, pressure, and residence time to form alkylate;
   (d) passing the reaction effluent containing alkylate from step (c) upwardly into a settling zone to separate an HF acid phase and a hydrocarbon phase containing said alkylate product; and
   (e) recycling a portion of said separated hydrocarbon phase to each point of introduction of said olefin in step (a) and step (b) so that the recycle hydrocarbon phase can function as a reaction heat removal liquid when the alkylation reaction is occurring.

2. A process according to claim 1 wherein said isoparaffin is isobutane, said lighter olefin is propylene, and said heavier olefin is a butylene.

3. A process according to claim 1 wherein the amount of hydrocarbon recycled to each point of olefin introduction is in the range of 10:1 to 100:1 of recycle hydrocarbon to olefin volume ratio at the inlet end of said reaction zone and the volume ratio of recycle hydrocarbon to different olefin at points downstream is in the range of about 2:1 to about 50:1.

4. A process according to claim 1 wherein a portion of the hydrocarbon phase separated in (d) is passed to fractionation to separate said alkylate product from unreacted isoparaffin for recycle to (a).

5. A process according to claim 1 wherein isobutane is alkylated with propylene introduced at said lower end portion and with a butylene introduced at said intermediate section, the reactor inlet temperature is in the range of about 60° F. to about 120° F., the pressure is sufficient to maintain liquid phase conditions, the reactor outlet temperature is in the range of about 40° F. to about 100° F., the isobutane to olefin ratio is in the range of about 10:1 to about 100:1, and the HF to total hydrocarbon volume ratio is in the range of about 5:1 to about 1:5.

6. A process according to claim 1 wherein the separated hydrocarbon recycled to olefin in (a) is heated prior to introduction into said reactor and the separated hydrocarbon recycled to olefin in (b) is cooled prior to introduction into said reactor.

* * * * *